United States Patent [19]

Bobee et al.

[11] Patent Number: 4,908,214
[45] Date of Patent: Mar. 13, 1990

[54] PHARMACEUTICAL TABLET FOR THE TREATMENT OF URAEMIA

[75] Inventors: Jean-Marc Bobee; Christian Melin, both of Verrières le Buisson, France

[73] Assignee: Synthelabo, Paris, France

[21] Appl. No.: 204,813

[22] Filed: Jun. 10, 1988

[30] Foreign Application Priority Data

Jul. 23, 1987 [FR] France .................. 87 10406

[51] Int. Cl.$^4$ ............................. A61K 9/38
[52] U.S. Cl. .................. 424/477; 424/475; 424/480; 424/482
[58] Field of Search .......... 424/482, 480, 502, 477, 424/475; 426/656

[56] References Cited

U.S. PATENT DOCUMENTS

| | | | |
|---|---|---|---|
| 3,079,303 | 2/1963 | Raff | 424/500 |
| 4,079,125 | 3/1978 | Sidos | 424/482 X |
| 4,228,099 | 10/1980 | Walser | 260/501.11 |
| 4,296,127 | 10/1981 | Walser | 424/319 |
| 4,320,146 | 3/1982 | Walser | 424/319 |
| 4,351,337 | 9/1982 | Sidman | 424/497 X |
| 4,352,814 | 10/1982 | Walser | 424/273 R |
| 4,675,339 | 6/1987 | Inoue et al. | 424/497 X |
| 4,713,245 | 12/1987 | Ando et al. | 424/482 X |
| 4,752,619 | 6/1988 | Walser et al. | 514/564 |

FOREIGN PATENT DOCUMENTS

| | | |
|---|---|---|
| 0184999 | 6/1986 | European Pat. Off. . |
| 0227545 | 7/1987 | European Pat. Off. . |
| 2315916 | 1/1977 | France . |
| 2419723 | 4/1979 | France . |
| 2454434 | 11/1980 | France . |

OTHER PUBLICATIONS

Voigt, R., "Lehrbuch der pharmazeutischen Technologie", 1975, pp. 213-218.

Primary Examiner—Thurman K. Page
Attorney, Agent, or Firm—Fleit, Jacobson, Cohn, Price, Holman & Stern

[57] ABSTRACT

A tablet constituted by (1) a core comprising a mixture of salts formed by a basic $\alpha$-amino acids and $\alpha$-keto analogues of branched-chain essential amino acids and (2) a gastroresistant or gastrosoluble coating.

16 Claims, No Drawings

PHARMACEUTICAL TABLET FOR THE TREATMENT OF URAEMIA

The present invention relates to pharmaceutical compositions useful in the treatment of uraemia.

Compositions consisting of mixtures of salts formed by α-keto acids and basic amino acids are useful as nutritional supplements for the treatment of chronic renal insufficiency.

Salts of basic α-amino acids and of α-keto analogues of branched-chain essential amino acids have been described in French Patents 79/06,533 (2,419,723) and 80/08,318 (2,454,434).

Compositions containing mixtures of several of these salts, and which can also contain L-tyrosine, L-threonine and calcium α-hydroxy-γ-methylthiobutyrate, have been described in European Patent Application No. 86 402 806.3.

Compositions containing mixtures of several salts of basic α-amino acids and of α-keto analogues of branched-chain essential amino acids, and also containing L-tyrosine, L-threonine, L-tryptophan and calcium α-hydroxy-γ-methylthiobutyrate, have been described in European Patent Application No. 88 401 261.8.

Compositions containing mixtures of several of these salts, and which can also contain L-tyrosine, L-threonine and calcium α-hydroxy-γ-methylthiobutyrate, and optionally tryptophan, may be presented in the form of a powder or granules which can be dissolved or suspended in water or a drink such as grapefruit or orange juice.

However, it has become apparent that compositions in the form of a powder or granules are not perfectly stable at room temperature; in addition they have an unpleasant taste and smell, which upsets the patients and limits compliance with the treatment.

We have developed a gastroresistant or gastrosoluble coated tablet formulation which possesses much greater stability than the powder or granules and which is odourless and tasteless, making the compositions more acceptable to the patients.

The present invention therefore provides a tablet constituted (1) by a core comprising a mixture of salts formed by basic α-amino acids and by α-keto analogues of branched-chain essential amino acids and (2) by a gastroresistant or gastrosoluble coating.

The core may also contain, for example, L-tyrosine, L-threonine and calcium DL-α-hydroxy-γ-methylthiobutyrate and optionally L-tryptophan.

The core may also contain, in addition to the active principles, various suitable excipients, for example, a binder, a disintegrating agent, a water-absorbing agent and a lubricant.

The respective quantities of the constituents of the core are generally as follows, by weight per 100 g of the core:
0.5 to 5% of binder,
2 to 20% of disintegrating agent,
0.5 to 15% of water-absorbing agent, and
0.5 to 3% of lubricant,
the remaining weight of the core being the mixture of active principles.

The mixture of active principles is a mixture of salts of basic α-amino acids and of α-keto analogues of branched-chain essential amino acids, generally containing all or part of the following constituents in the following proportions (expressed as a percentage by weight of the mixture):

| | |
|---|---|
| α-ketoisovalerate (or ketovaline) | 5–20 |
| α-ketoisocaproate (or ketoleucine) | 5–15 |
| α-keto-β-methylvalerate (or ketoisoleucine) | 5–15 |
| L—ornithine | 15–25 |
| L—lysine | 10–25 |
| L—histidine | 1–10 |
| L—threonine | 1–10 |
| L—tyrosine | 5–20 |
| L—tryptophan | 0–5 |
| calcium DL-α-hydroxy-γ-methylthiobutyrate | 1–5 |

The core can comprise, for example, 250 to 1000 mg of the mixture of active principles.

The binder can be, for example a cellulose derivative such as hydroxypropylmethylcellulose (HPMC) or carboxy-methyl-cellulose. The disintegrating agent can be, for example, a polysaccharide derivative such as carboxymethylstarch.

The water-absorbing agent can be, for example, silica gel, and the lubricant can be, for example, magnesium stearate.

The coating generally represents from 5 to 20% of the weight of the core. It may, for example, be produced by spraying, onto the core, an organic solution containing a film-forming agent to form the coating, and optionally one or more colouring agents, a plasticizer and a filler.

The coating solution can, for example, contain from 2 to 20% (weight/volume) of a film-forming agent, from 0 to 10% of a colouring agent, from 0 to 5% of a plasticizer and from 0 to 10% of a filler, the remaining part to 100 ml of the solution being, for example, a mixture of suitable proportions of an alcoholic solvent and a clorinated solvent or an aqueous solution.

The quantity of coating solution sprayed on 100 g of core is generally from 50 to 150 ml, according to the chemical nature of the film-forming agent used.

The coating can be gastrosoluble or gastroresistant. By way of example, the gastrosoluble coating can be cationic polymerisate of dimethylaminoethyl methacrylate and of other neutral esters of methacrylic acid or hydroxypropylmethyl-cellulose.

The gastroresistant coating can be, for example, hydroxypropylmethylcellulose (HPMC) phthalate.

The colouring agent can be, for example, an organic suspension of titanium dioxide, and the plasticizer can be, for example, diethylpthalate or an acetylated monoglyceride.

The filler can be, for example, magnesium stearate or talc.

The solvent preferably consists of a 50:50 mixture of methylene chloride and ethanol.

The Examples which follow further illustrate the invention:

EXAMPLE 1

Gastrosoluble coated tablet

| Core: Active principles (AP) | Theoretical percentage composition (in g) | Composition of a tablet containing a 770-mg dose of AP (in mg) |
|---|---|---|
| L—tyrosine | 18.006 | 150.71 |
| L—threonine | 8.879 | 74.31 |
| L—tryptophan | 0.487 | 4.16 |

| Core: Active principles (AP) | Theoretical percentage composition (in g) | Composition of a tablet containing a 770-mg dose of AP (in mg) |
|---|---|---|
| L—ornithine α-keto-β-methylvalerate | 18.245 | 152.71 |
| L—ornithine α-keto-isovalerate | 8.636 | 72.28 |
| L—Lysine α-keto-isocaproate | 19.223 | 160.89 |
| L—Lysine α-keto-isovalerate | 9.123 | 76.35 |
| L—histidine α-keto-isocaproate.H$_2$O | 6.027 | 50.44 |
| Ca DL-α-hydroxy-γ-methylthiobutyrate | 3.364 | 28.15 |
| Core excipients | | |
| Carboxymethylstarch (PRIMOJEL MD) | 5 | 41.85 |
| Silica gel | 2 | 16.74 |
| Magnesium stearate | 1 | 8.37 |
| | 100 | 836.96 |
| Coating solution | | |
| EUDRAGIT E 100* | 5 g | |
| Talc | 3.5 g | |
| Magnesium stearate | 1 g | |
| Colouring (SEPISPERSE WHITE K 7001) | 5 g | |
| Solvents: ethanol 50 CH$_2$Cl$_2$ 50 q.s. | 100 ml | |

NB: 60 ml of coating solution for 100 g of tablet (equivalent to 3% of film-forming agent with respect to the weight of the core).

*EUDRAGIT E = cationic polymerisate of dimethylaminoethyl methacrylate and of other neutral esters of methacrylic acid.

EXAMPLE 2

Gastroresistant coated tablet

| Core: Active principles | Theoretical percentage compostion (in g) | Composition of a tablet containing an 850-mg dose of AP (in mg) |
|---|---|---|
| L—tyrosine | 18.17 | 167.87 |
| L—threonine | 8.96 | 82.78 |
| L—ornithine α-keto-β-methylvalerate | 18.42 | 170.18 |
| L—ornithine α-keto-isovalerate | 8.72 | 80.56 |
| L—lysine α-keto-isocaproate | 19.40 | 179.24 |
| L—lysine α-keto-isovalerate | 9.21 | 85.09 |
| L—histidine α-keto-isocaproate | 5.72 | 52.85 |
| Ca DL α-hydroxy-γ-methylthiobutyrate | 3.40 | 31.41 |
| Core excipients | | |
| Carboxymethylstarch (PRIMOJEL MD) | 5 | 46.20 |
| Silica gel | 2 | 18.48 |
| Magnesium stearate | 1 | 9.24 |
| | 100 | 923.90 |
| Coating solution | | |
| HPMC phthalate (HP 55 - SEPPIC) | 10 | 92.39 |
| Diethyl phthalate | 2 | 18.48 |
| Colouring (SEPISPERSE YELLOW AP 3012) | 5 | 23.10 |
| Solvents: .ethanol 50 .CH$_2$Cl$_2$ 50 q.s. | 100 ml | |

NB: 100 ml of coating solution for 100 g of tablet (equivalent to 10% of film-forming agent with respect to the weight of the core).

We claim:

1. A tablet consisting of (1) a core comprising a mixture of salts formed from basic α-amino acids and α-keto analogues of branched-chain essential amino acids and (2) a gastroresistant or gastrosoluble coating.

2. A tablet according to claim 1 wherein the core additionally comprises L-tyrosine, L-threonine and calcium DL-α-hydroxy-γ-methylthiobutyrate.

3. A tablet according to claim 1 wherein the core additionally comprises L-tryptophan.

4. A tablet according to claim 1 wherein the core also comprises a binder, a disintegrating agent, a water-absorbing agent and a lubricant.

5. A tablet according to claim 4 wherein the binder is a cellulose derivative.

6. A table according to claim 5 wherein the binder is hydroxypropylmethylcellulose or carboxymethylcellulose.

7. A tablet according to claim 4 wherein the disintegrating agent is a polysaccharide derivative.

8. A tablet according to claim 7 wherein the disintegrating agent is carboxymethylstarch.

9. A tablet according to claim 4 wherein the water-absorbing agent is silica gel.

10. A tablet according to claim 4 wherein the lubricant is magnesium stearate.

11. A tablet according to claim 1 wherein the coating comprises a film forming agent, one or more colouring agents, a plasticizer and a filler.

12. A tablet according to claim 1 wherein the coating comprises a cationic polymerisate of dimethylaminoethyl methacrylate and of other neutral esters of methacrylic acid.

13. A tablet according to claim 1 wherein the coating comprises hydroxypropylmethyl-cellulose.

14. A tablet according to claim 1 wherein the coating comprises hydroxypropylmethyl-cellulose phthalate.

15. A process for preparing a tablet as defined in claim 1 wherein an organic solution containing a film forming agent to form the coating is sprayed onto the core.

16. A process according to claim 15 wherein the organic solution comprises methylenechloride and ethanol.

* * * * *